(12) United States Patent
Breazeale

(10) Patent No.: US 9,877,785 B1
(45) Date of Patent: Jan. 30, 2018

(54) SURGICAL DRAPE SUPPORT

(71) Applicant: Richard Breazeale, Signal Mountain, TN (US)

(72) Inventor: Richard Breazeale, Signal Mountain, TN (US)

( * ) Notice: Subject to any disclaimer, the term of this patent is extended or adjusted under 35 U.S.C. 154(b) by 650 days.

(21) Appl. No.: 14/467,155

(22) Filed: Aug. 25, 2014

(51) Int. Cl.
*A61B 19/08* (2006.01)
*A61M 16/06* (2006.01)

(52) U.S. Cl.
CPC .......... *A61B 19/08* (2013.01); *A61M 16/0666* (2013.01); *A61B 2019/084* (2013.01)

(58) Field of Classification Search
CPC ............................... A61M 25/02; A61B 46/40
See application file for complete search history.

(56) References Cited

U.S. PATENT DOCUMENTS

| | | | |
|---|---|---|---|
| 3,347,544 A * | 10/1967 | Uffenorde | A61B 6/0421 128/200.24 |
| 3,403,677 A | 10/1968 | Struve | |
| 3,464,411 A * | 9/1969 | Martinez | A61M 16/06 128/200.24 |
| 3,530,515 A | 9/1970 | Jacoby | |
| 3,859,993 A | 1/1975 | Bitner | |
| 4,122,848 A | 10/1978 | Carpel | |
| 4,321,917 A | 3/1982 | Campbell | |
| 4,465,066 A | 8/1984 | Carpel | |
| 4,699,131 A * | 10/1987 | Crook | A61F 9/007 128/200.24 |
| 4,739,753 A | 4/1988 | Brehm | |
| 4,971,037 A | 11/1990 | Pelta | |
| D318,920 S | 8/1991 | Bruhl, Jr. | |
| 5,488,944 A | 2/1996 | Kennedy | |
| 5,730,153 A | 3/1998 | Chang et al. | |
| 6,302,109 B1 | 10/2001 | Parnes | |
| 6,374,439 B2 | 4/2002 | Helmbrock et al. | |
| 6,871,651 B2 | 3/2005 | Lanier | |
| 7,114,499 B2 | 10/2006 | Davis | |
| 8,397,725 B2 * | 3/2013 | Slaker | A61M 16/06 128/205.26 |
| 8,439,043 B2 | 5/2013 | Davis | |
| 8,464,721 B2 | 6/2013 | Davis | |
| 2011/0315150 A1 | 12/2011 | Bream, Jr. | |

FOREIGN PATENT DOCUMENTS

| | | |
|---|---|---|
| JP | 2001170101 | 6/2001 |
| JP | 2010284385 | 12/2010 |
| JP | 2012161542 | 8/2012 |

* cited by examiner

*Primary Examiner* — Tarla Patel
(74) *Attorney, Agent, or Firm* — Matthew M. Googe; Robinson IP Law, PLLC

(57) ABSTRACT

A surgical drape support for maintaining a surgical drape above a patient's face is provided. The surgical drape includes a base member positioned adjacent to a top portion the patient's head, the base member including a first end and a second end, a first connector secured adjacent a first end of the base member, a second connector secured adjacent a second end of the base member, and an arch support member extending from the first connector, across the patient's face, and to the second connector. The arch support member extends diagonally across the patient's face for supporting the surgical drape above the patient's mouth while allowing the drape to be positioned directly adjacent one of the patient's eyes.

12 Claims, 8 Drawing Sheets

SURGICAL DRAPE SUPPORT

FIELD

This disclosure relates to the field of surgical drapes. More particularly, this disclosure relates to a support for maintaining a surgical drape off of the face of a patient during eye or other facial surgery.

BACKGROUND

Surgical drapes are frequently used during surgical procedures to protect an area around a surgical procedure from infection. A surgical drape is typically positioned adjacent to and around an area of a surgical procedure to create a barrier between the surgical site and surrounding tissue and to also control any fluid that results from the surgical procedure.

However, when drapes are used in procedures involving a patient's face, such as ophthalmic procedures, the drape often creates a feeling of claustrophobia and may make breathing difficult because the drape is positioned against the nose, mouth, and other areas of a patient's face during a procedure. This may be particularly problematic when a patient is awake and alert during a procedure.

While attempts have been made to create a drape support that maintains a drape above a patient's face, these supports are typically complex. Further, previous attempts at creating a drape support are not configured to maximize clearance between a patient's mouth and a drape depending on a side of the patient's face being operated on.

What is needed, therefore, is a surgical drape support configured to support a drape above a patient's face and maximize room between the drape and the patient's face based on a side of the patient's face undergoing a surgical procedure.

SUMMARY

The above and other needs are met by an apparatus for supporting a surgical drape above a patient's face. The drape support apparatus includes a base member positioned adjacent to a top portion the patient's head, the base member including a first end and a second end, a first connector secured adjacent a first end of the base member, a second connector secured adjacent a second end of the base member, and an arch support member extending from the first connector, across the patient's face, and to the second connector. The arch support member extends diagonally across the patient's face for supporting the surgical drape above the patient's mouth while allowing the drape to be positioned directly adjacent one of the patient's eyes.

In one embodiment, the base member is substantially U-shaped. In another embodiment, the second connector further comprises a sleeve for engaging one of the first end or second end of the base member such that the second connectors is maintained at a position that is substantially further down the patient's face relative to the first connector.

In one embodiment, the first connector and second connector are removably secured to the base member such that the first connector and second connector may be swapped from the first end of the base member to the second end of the base member and vice versa.

In another embodiment, the drape support further includes a surgical drape positioned over the arch support member.

In yet another embodiment, the first connector is slidably secured to the base member such that a position of the first connector may be adjusted along the base member.

In one embodiment, the arch support member is in fluid communication with an oxygen supply. In another embodiment, the arch support member includes a plurality of apertures form along an underside of the arch support member for emitting oxygen from an oxygen supply towards a patient's face. In yet another embodiment, the arch support member further includes a connector for connecting a nasal cannula to the arch support member such that oxygen from an oxygen supply flows into the nasal cannula.

In another aspect, embodiments of the disclosure provide a surgical drape support for maintaining a surgical drape above a patient's face. The surgical drape support includes a a base member positioned adjacent to and surrounding the patient's face, wherein the base member is positioned adjacent a top portion the patient's head, the base member including a first end and a second end, a first connector slidably secured adjacent a first end of the base member, the first connector including a sleeve and a first extension member extending substantially upward from the patient's face, a second connector secured adjacent a second end of the base member, the second connector including a second extension member extending substantially upward from the patient's face, an arch support member secured to the first connector at a first end and the second connector at a second end, and a surgical drape placed over the arch support member. The first connector is maintained at a position substantially further down a patient's head relative to the second connector. Further, the arch support member extends diagonally across the patient's face from the first connector to the second connector for supporting the surgical drape above the patient's mouth while allowing the drape to be positioned directly adjacent one of the patient's eyes.

In one embodiment, the first connector and second connector are removably secured to the base member such that the first connector and second connector may be swapped from the first end of the base member to the second end of the base member and vice versa.

In another embodiment, the second connector is slidably engaged with the second end of the base support such that the second connector is slidably adjustable along a length of the base support.

In yet another aspect, embodiment of the disclosure provide a method of securing a surgical drape above a patient's face such that a mouth and portion of the face of the patient are substantially unobstructed by the surgical drape. The method includes providing a U-shaped base member adjacent a top portion of a patient's head, providing a drape support comprising a first connector, a second connector and an arch support member, positioning the first connector substantially halfway along a length of the patient's face, positioning the second connector adjacent a bottom portion of the patient's face, securing the arch support member between the first connector and the second connector, adjusting a position of the first connector such that the arch support member extends across the patient's face and substantially above a mouth of the patient, and laying the surgical drape over the arch support member above the patient's face.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

A surgical drape support is provided that is configured to advantageously support a surgical drape above a patient's face while allowing the drape to contact a portion of the patient's face adjacent a surgical site to create a protective barrier around the surgical site. The surgical drape support is adjustable such that a position of a surgical drape may be altered based on a side of the patient's face undergoing a surgical procedure.

Figure 1:
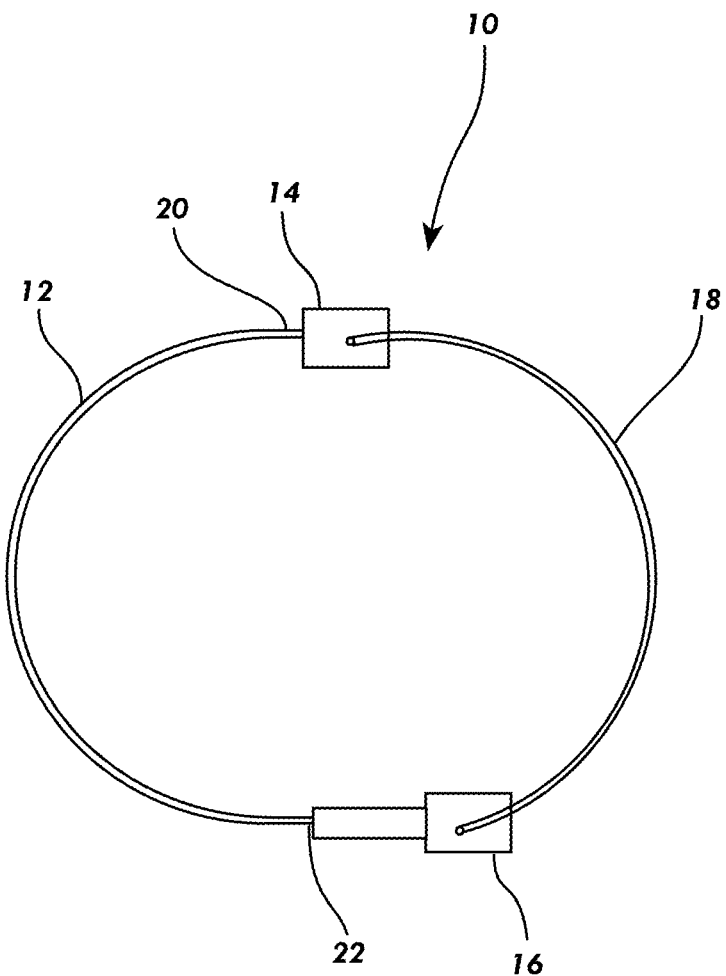
FIG. 1 is a top view of a surgical drape support according to one embodiment of the disclosure.

FIG. 1 shows a basic embodiment of a surgical drape support 10 for supporting a surgical drape above a patient's face. The surgical drape support 10 includes a base member 12, a first connector 14 secured to the base member 12, a second connector 16 secured to the base member 12, and an arch support member 18 extending between the first connector 14 to the second connector 16.

The base member 12 is preferably substantially U-shaped and terminates at a first end 20 and a second end 22. The U-shaped base member 12 is preferably formed to substantially conform around a top of the patient's head. In a preferable embodiment, the U-shaped base member 12 is a structural component of a hospital bed or other surface on which the patient is laying. For example, eye surgery stretchers such as those available from Stryker Corporation may include a contoured headpiece positioned adjacent a patient's head during procedures involving the patient's eye. The U-shaped base member 12 is preferably secured to the eye surgery stretcher to support the first connector 14 and second connector 16 secured thereto.

While the base member 12 is preferably U-shaped, it is also understood that the base member 12 may be circular, rectangular or other like shapes such that the base member 12 is positionable around a patient's face. Further, while the U-shaped base member 12 is preferably a structural component of the hospital bed, it is also understood that the base member 12 may be a separate component from a hospital bed and configured to be readily secured adjacent a patient's face during an eye procedure. The base member 12 is preferably formed of a plastic, polymer, stainless steel, or other like materials.

Figure 2:
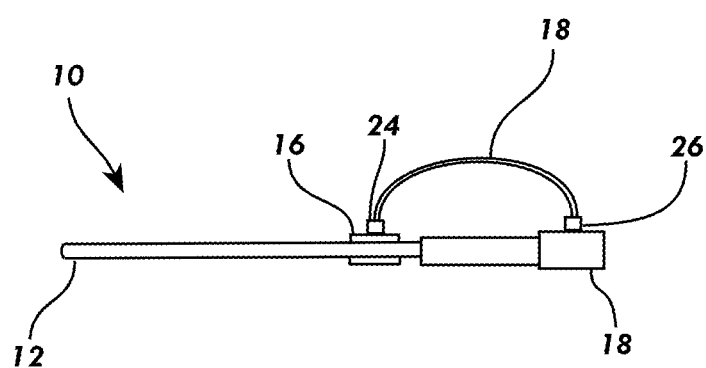
FIG. 2 is a side view of a surgical drape support according to one embodiment of the disclosure.

The first connector 14 is secured adjacent the first end 20 of the base member 12 and the second connector 16 is secured adjacent the second end 22 of the base member 12. Referring now to FIG. 2, the first connector 14 includes a first extension 24 for engaging an end of the arch support member 18. Similarly, the second connector 16 includes a second extension 26 for engaging another end of the arch support member 18. The second connector 16 also includes a sleeve 17 (FIG. 3) secured to the second connector 16 for engaging the second end 22 of the base member 12. The sleeve 17 maintains the second connector 16 at a substantially lower position adjacent the patient's face relative to the first connector 14, such as by positioning the second connector 16 adjacent a nose or mouth of the patient.

The arch support member 18 extends from the first extension 24 of the first connector 14 to the second extension 26 of the second connector 16. The first extension 24 and second extension 26 extend substantially perpendicular to the base member 12 and substantially parallel to one another such that the arch support member 18 extends upwardly from the base member 12 away and towards a center of a patient's face.

Figure 3:
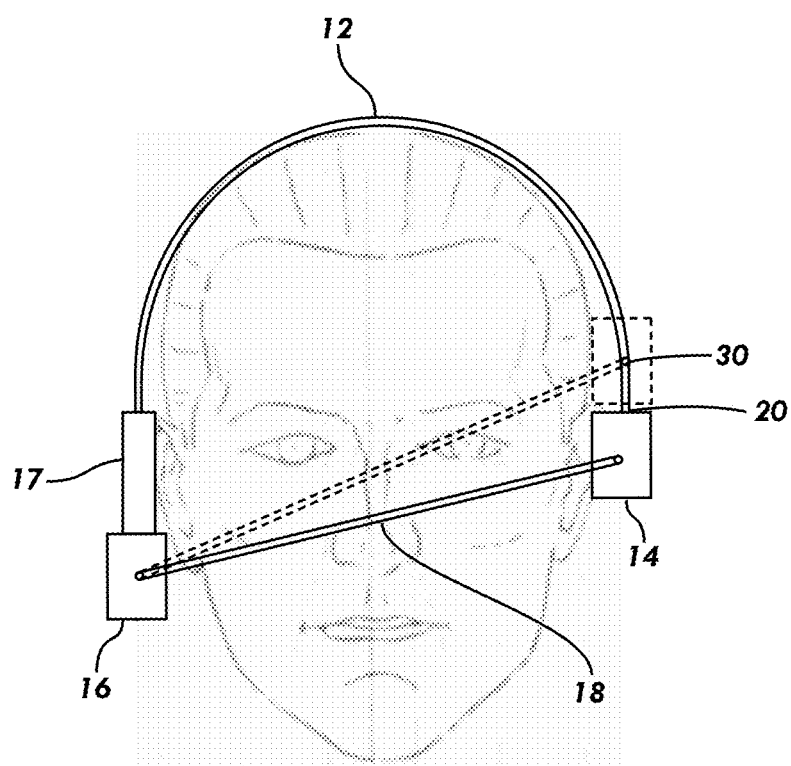
FIG. 3 illustrates a surgical drape support according to one embodiment of the disclosure.

Referring now to FIG. 3, the first connector 14 is preferably slidably secured to the base member 12 such that a position of the first connector 14 may be adjusted along a length of the base member 12. For example, in a first position 28 the first connector 14 is adjacent the first end 20 of the base member 12 and the arch support member 18 extends diagonally across the patient's face. The first connector 14 is slidably adjusted along the base member 12 to a second position 30 such that a position of the arch support member 18 across the patient's face is changed. The first connector 14 is preferably T-shaped such that the first connector may slidably engage the base member 12 while the first extension 24 extends therefrom to engage the arch support member 18 (FIG. 5).

Figure 4:
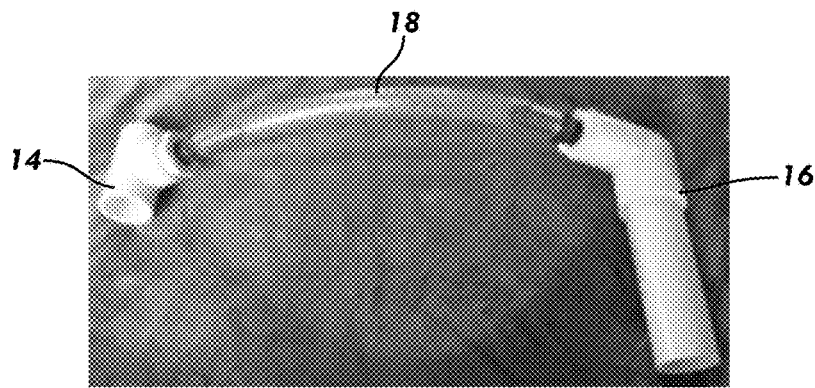
FIGS. 4-6 illustrate a surgical drape support according to one embodiment of the disclosure.
Figure 5:
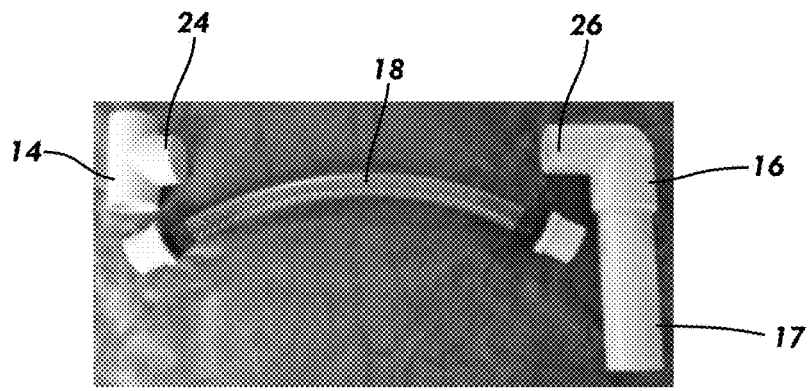
Figure 6:
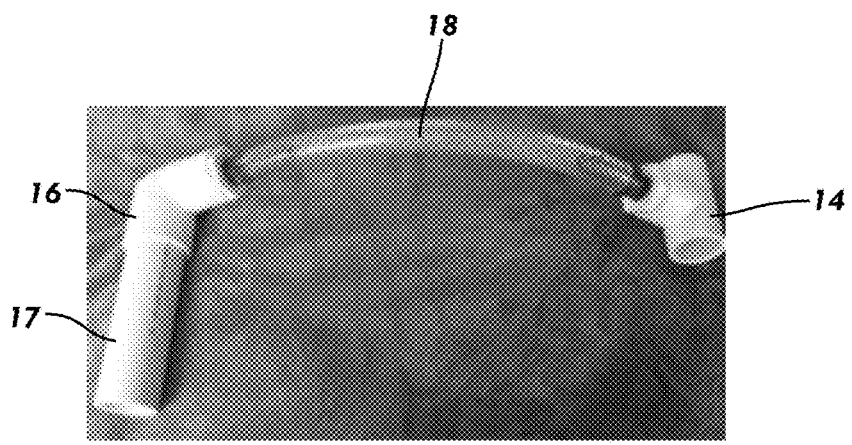

Referring now to FIGS. 4-6, the surgical drape support 10 of the present disclosure is readily reconfigurable from a position such that a surgical drape is supported above a patient's face while allowing the drape to be positioned adjacent one eye of the patient during surgery to a position where the surgical drape is supported above the patient's face while allowing the drape to be positioned adjacent an other eye of the patient.

For example, in FIG. 4 the surgical drape support 10 is shown in a first configuration where the arch support member 18 would extend diagonally from a lower right portion of a patient's face to an upper left portion of a patient's face such that a surgical drape is supported above a patient's mouth and left side of a patient's face while being allowed to lay against a patient's face adjacent a right eye of the patient, such as the configuration illustrated in FIG. 3. Such a configuration is desirable when a surgical procedure is being performed on a patient's right eye.

As illustrated in FIG. 5, the arch support member 18 is removable from the first connector 14 and the second connector 16. Further, the first connector 14 and the second connector 16 are removable from the U-shaped base member 12. For example, the first connector 14 and the second connector 16 may be slidably or threadably engaged with the first end 20 and second end 22 of the base member 12. While the above description contemplates removing the arch support member 18 from the first connector 14 and second connector 16, alternatively the arch support member 18 may remain secured to the first connector 14 and second connector 16 when the first connector 14 and second connector 16 are removed from the base member 12.

Figure 7:
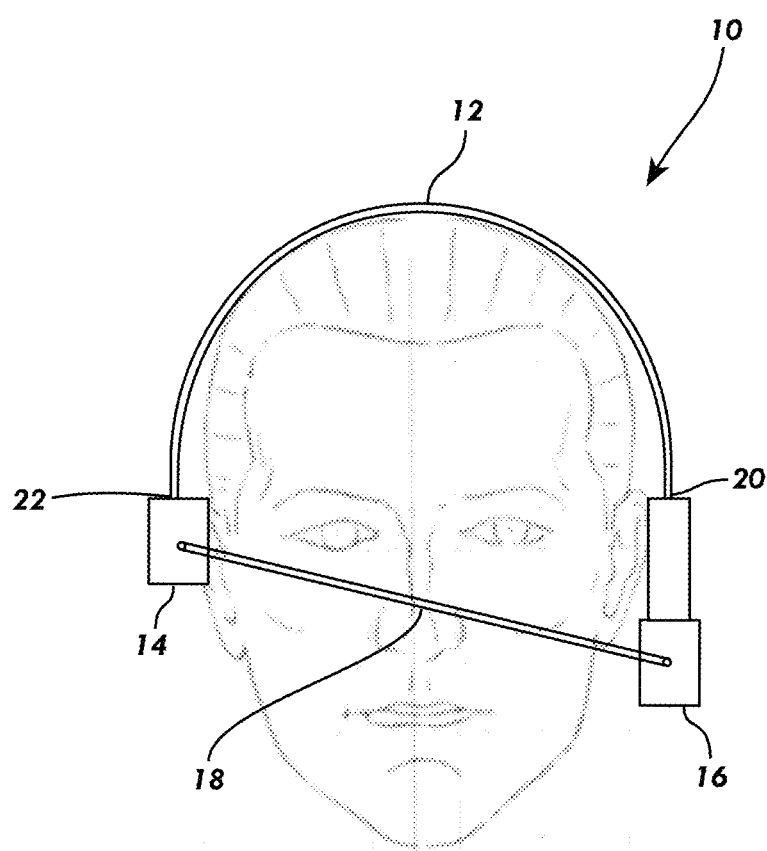
FIG. 7 illustrates a surgical drape support according to one embodiment of the disclosure.

Referring now to FIG. 6, the first connector 14 and second connector 16 are "swapped" such that the first connector 14 is now secured to the base member 12 adjacent the second end 22 of the base member 12 and the second connector 16 is secured adjacent the first end 20 of the base member 12. The arch support member 18 is secured to the first connector 14 and second connector 16 and is positioned to extend substantially diagonally across a patient's face and to support a drape above a patient's mouth while allowing a drape to contact the patient's face adjacent the patient's eye. Specifically, the configuration of FIG. 7 is preferable in preparation for a surgical procedure on a left eye of a patient wherein a drape is allowed to contact a patient's face adjacent a left eye of the patient.

Figure 8:
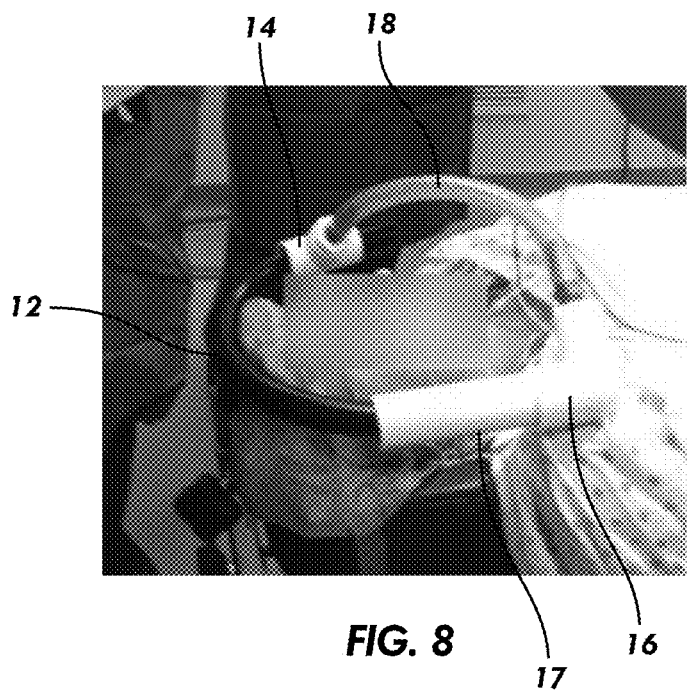
FIGS. 8 and 9 show a surgical drape support secured adjacent a patient's face according to one embodiment of the disclosure.
Figure 9:
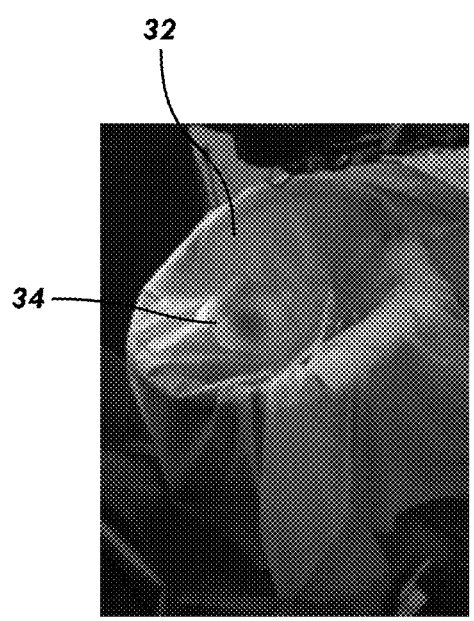

Referring now to FIG. 8, when in use the surgical drape support 10 is positioned and supported adjacent a patient's face such that the base member 12 is positioned around the patient's face. The first connector 14, second connector 16, and arch support member 18 are positioned in a desired location based on an eye of a patient being operated on. FIG. 8 illustrates the drape support 10 configured for an operation on a right eye of a patient.

Figure 10:
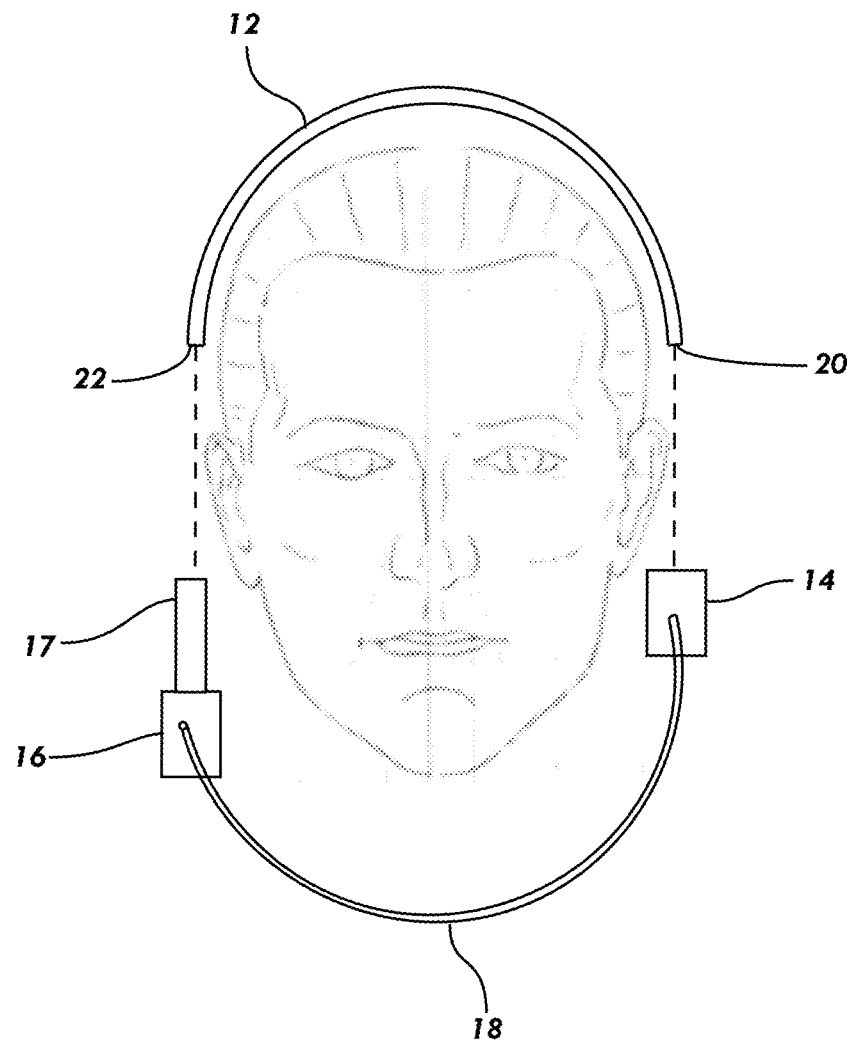
FIG. 10 illustrates assembly of a surgical drape support according to one embodiment of the disclosure.

FIG. 10 illustrates assembly of the drape support 10 to a base member 12 that is part of a hospital bed or other surface supporting a patient. The base member 12 is positioned such that the base member 12 is substantially adjacent a top of a patient's head and such that the first end 20 and second end 22 extend along sides of a patient's head. The first connector 14, second connector 16 and attached sleeve 17 are slidably engaged with the first end 20 and second end 22 of the base member 12 after the base member 12 is positioned in a desired location adjacent a patient's head.

After positioning the drape support 10 adjacent a patient's face, a surgical drape 32 is placed over the drape support 10. When the surgical drape 32 is placed over the drape support 10, the arch support member 18 maintains the drape above the patient's mouth. Further, an aperture 34 may be formed in the drape 32 to allow access to the patient's eye while maintaining the drape 32 adjacent the patient's eye.

In one embodiment, a kit of components are provided for fitting the drape support 10 to a hospital bed or other supporting surface wherein the bed already includes a suitable base member 12 secured to the bed. The kit includes the first connector 14, second connector 16 and attached sleeve 17, and the arch support member 18 extending between the first and second connectors 14 and 16. The first connector 14 and second connector 16 may be configured to adapt to base members 12 having various sizes and shapes. When the kit is installed on the base member 12, the drape support 10 is configured to be adjustable such that a surgical drape may be supported above either a patient's left eye or right eye depending on a procedure to be performed.

Figure 11:
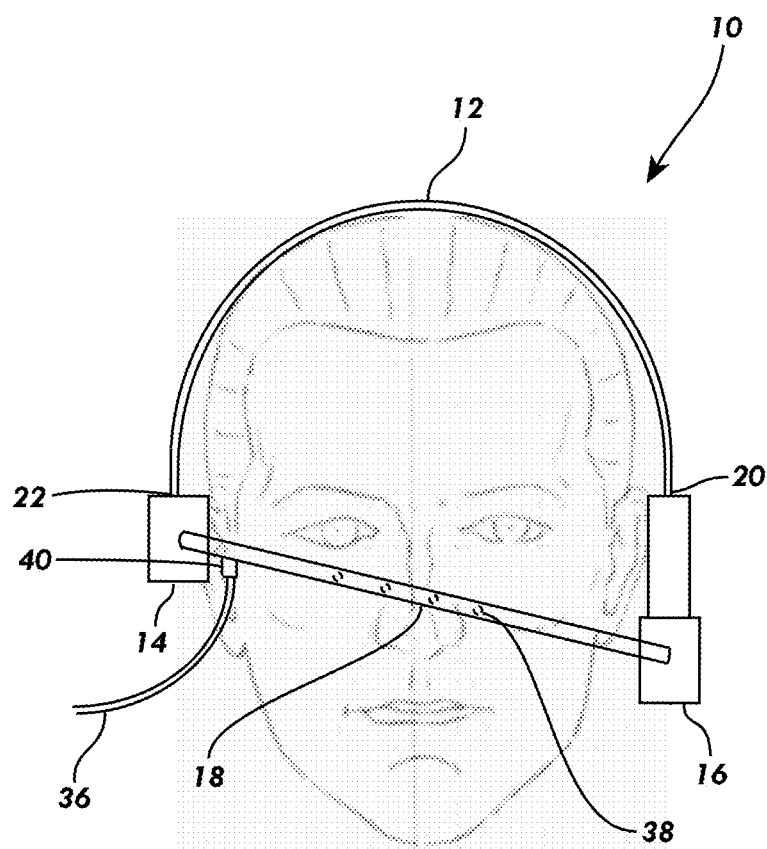
FIG. 11 illustrates a surgical drape support in communication with an oxygen supply according to one embodiment of the disclosure.

In another embodiment, the drape support 10 is configured to enhance a flow of oxygen adjacent a patient's face to further reduce any claustrophobia experienced by the patient. FIG. 11 illustrates an embodiment of a surgical drape support 10 that is configured to induce a flow of oxygen adjacent a patient's face. The arch support member 18 is in fluid communication with an external oxygen source 36, such as an oxygen tank or hose in communication with a hospital oxygen supply system. The external oxygen source 36 may be connected either directly to the arch support member 18, as shown in FIG. 11, or alternatively the external oxygen source may be connected to one or both of the first connector 14 and second connector 16 which may be in fluid communication with the arch support member 18.

The arch support member 18 may include a plurality of apertures 38 formed therethrough. The apertures 38 are formed along an underside of the arch support member 18 such that oxygen that flows out of the apertures 38 is directed towards a patient's face. The arch support 18 may be connected to and in fluid communication with an oxygen supply through a connector 40 that allows an oxygen supply to be readily connected to or removed from the arch support member 18.

During an eye procedure, a nasal cannula is typically inserted into nostrils of a patient to provide oxygen during the procedure, particularly when a surgical drape is placed over the patient's face. When a nasal cannula is used during a procedure, tubing is positioned around a patient's face, such as looping tubing around a patient's ears, to move oxygen from an oxygen supply into a patient's nostrils. However, while a patient may receive oxygen through the nasal cannula, the patient may still feel claustrophobic due to a lack of air around the patient's face under the drape. By placing the arch support member 18 in fluid communication with an oxygen supply such that oxygen is emitted from the arch support member 18 from a plurality of apertures 38 towards a patient's face, an oxygen level of the patient is increased. Further, circulating oxygen from the arch support member 18 under the drape may help to cool a patient's face and to further maintain a drape off of the patient's face to reduce any feeling of claustrophobia.

Alternatively, the arch support member 18 may include a connector for connecting tubing of a nasal cannula to the arch support member 18. By securing a nasal cannula to the arch support member 18, substantially less tubing is bring oxygen to a patient's face. As such, tubing may only be required to extend from the arch support member 18 to a patient's nostrils, thereby alleviating a need to drape excess tubing around a patient's ears or other parts of a patient's face.

The surgical drape support 10 of the present disclosure provides a simple and adjustable mechanism for maintaining a drape above a patient's face while still allowing the drape to be positioned adjacent a surgery site. The drape support 10 advantageously maintains the drape above the patient's mouth to substantially reduce any feeling of claustrophobia and to ease any breathing difficulty of the patient. The substantially asymmetrical shape of the base member and arch support member maximize an amount of surgical drape that is maintained above the patient's face. Further, because the drape support is readily adjustable, the arch support member is easily adjusted to fit a variety of face and head shapes. Finally, the drape support is easily adapted for use with a variety of beds or other surfaces on which a surgical procedure may occur by adapting to an existing base support member of the bed or surface or fitting to a bed or surface that lacks a base member component.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A surgical drape support mountable on a hospital bed, the surgical drape support for maintaining a surgical drape above the patient's head, the surgical drape support comprising:
   a base member positioned adjacent to a top portion the patient's head, the base member located around a top portion of a patient's head and having a first end and a second end, wherein the base member is a structural component of the hospital bed;
   a first connector associated with the first end of the base member, the first connector extending perpendicular to the base member;
   a second connector associated with the second end of the base member, the second connector extending perpendicular to the base member, the second connector including a sleeve such that the second connector is spaced apart from the second end of the base member; and
   an arch support member extending from the first connector, across the patient's face, and to the second connector that is spaced apart from the second end of the base member;
   wherein the arch support member extends diagonally across the patient's face for supporting the surgical drape above the patient's mouth while allowing the drape to be positioned directly adjacent one of the patient's eyes.

2. The surgical drape support of claim 1, wherein the base member is substantially U-shaped.

3. The surgical drape of claim 1, wherein the first connector and second connector are removably secured to the base member such that the first connector and second connector may be swapped from the first end of the base member to the second end of the base member and vice versa.

4. The surgical drape support of claim 1 further comprising a surgical drape positioned over the arch support member.

5. The surgical drape support of claim 1, wherein the first connector is slidably secured to the base member such that a position of the first connector may be adjusted along the base member.

6. The surgical drape support of claim 1, wherein the arch support member is in fluid communication with an oxygen supply.

7. The surgical drape support of claim 6, wherein the arch support member includes a plurality of apertures form along an underside of the arch support member for emitting oxygen from an oxygen supply towards a patient's face.

8. A surgical drape support for maintaining a surgical drape above a patient's face, the surgical drape support comprising:
   a base member located around a top of the patient's face, the base member including a first end and a second end, wherein the base member is a structural component of the hospital bed;
   a first connector associated with the first end of the base member, the first connector including a sleeve and a first extension member extending perpendicular to the base member and substantially upward from the patient's face;
   a second connector associated with the second end of the base member, the second connector including a second extension member extending perpendicular to the base member and substantially upward from the patient's face, the second connector including a sleeve such that the second connector is spaced apart from the second end of the base member;
   an arch support member secured to the first connector at a first end and the second connector at a second end;
   and a surgical drape placed over the arch support member;
   wherein the first connector is maintained at a positioned substantially further down a patient's head relative to the second connector such that the arch support member extends diagonally across the patient's face from the first connector the second connector for supporting the surgical drape above the patient's mouth while allowing the drape to be positioned directly adjacent one of the patient's eyes.

9. The surgical drape of claim 8, wherein the first connector and second connector are removably secured to the base member such that the first connector and second connector may be swapped from the first end of the base member to the second end of the base member and vice versa.

10. The surgical drape of claim 8, wherein the second connector is slidably engaged with the second end of the base support such that the second connector is slidably adjustable along a length of the base support.

11. A kit of components for assembling a surgical drape support on a hospital bed, the kit comprising:
   a first connector configured to engage to a first end of a base member of the hospital bed, the base member located around a top portion of a patient's head, the first connector including a first extension member extending perpendicular to the base member and substantially upwardly from a patient's head, wherein the base member is a structural component of the hospital bed;
   a second connector configured to engage to a second end of the base member of the hospital bed, the second connector including a second extension member extending perpendicular to the base member and substantially upwardly from a patient's head;
   an arch support member secured at a first end to the first extension member of the first connector and at a second end to the second extension member of the second connector;
   wherein the first connector and second connector are positioned such that the arch support member extends substantially diagonally across a patient's face for supporting a surgical drape above the patient's face during a surgical procedure, and further wherein a position of the arch support member is based on an eye of the patient undergoing a surgical procedure.

12. A method of securing a surgical drape above a patient's face such that a mouth and portion of the face of the patient are substantially unobstructed by the surgical drape, the method comprising:
   providing a hospital bed including a structural U-shaped base member located around a top portion of a patient's head, the U-shaped base member having a first end and a second end;
   providing a drape support comprising a first connector, a second connector and an arch support member;
   positioning the first connector substantially halfway along a length of the patient's face, the first connector slidably associated with the first end of the U-shaped base member;

positioning the second connector adjacent a bottom portion of the patient's face, the second connector slidably associated with the second end of the U-shaped base member;
securing the arch support member between the first connector and the second connector;
adjusting a position of the first connector such that the arch support member extends across the patient's face and substantially above a mouth of the patient; and
laying the surgical drape over the arch support member above the patient's face.

* * * * *